(12) United States Patent
Rosenberg et al.

(10) Patent No.: US 9,381,322 B2
(45) Date of Patent: *Jul. 5, 2016

(54) SYSTEMS AND METHODS FOR ANCHORING MEDICAL DEVICES

(71) Applicant: INTERRAD Medical, Inc., Plymouth, MN (US)

(72) Inventors: Michael S. Rosenberg, Eagan, MN (US); Mark R. Christianson, Plymouth, MN (US); Kyle P. Taylor, Brooklyn Park, MN (US); Andrew T. Forsberg, Plymouth, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/594,516

(22) Filed: Jan. 12, 2015

(65) Prior Publication Data

US 2015/0133867 A1 May 14, 2015

Related U.S. Application Data

(63) Continuation of application No. 13/705,651, filed on Dec. 5, 2012, now Pat. No. 8,956,329, which is a continuation of application No. 12/893,783, filed on Sep. 29, 2010, now Pat. No. 8,343,108.

(51) Int. Cl.
*A61M 25/02* (2006.01)
*A61M 39/02* (2006.01)
*A61M 25/04* (2006.01)

(52) U.S. Cl.
CPC ............... *A61M 25/02* (2013.01); *A61M 25/04* (2013.01); *A61M 39/0208* (2013.01);

(Continued)

(58) Field of Classification Search
CPC ............... A61M 2025/024; A61M 2025/0246; A61M 25/02; A61M 2025/0266; A61M 2025/0253; A61M 2025/026; A61M 2025/028; A61M 2025/0286; A61M 2039/0223; A61M 2039/0232; A61M 25/04; A61M 39/0208; A61M 39/0261; A61M 39/0247
See application file for complete search history.

(56) References Cited

U.S. PATENT DOCUMENTS 2,525,398 A 10/1950 Collins
3,039,468 A 6/1962 Price (Continued)

FOREIGN PATENT DOCUMENTS

WO WO 91/15254 10/1991
WO WO 2004/026152 4/2004

(Continued)

OTHER PUBLICATIONS

Johnson & Johnson web page printout, "The EndoANCHOR Features and Benefits" printed Sep. 13, 2005, 2 pages.

(Continued)

*Primary Examiner* — Kami A Bosworth
*Assistant Examiner* — Brandy S Lee
(74) *Attorney, Agent, or Firm* — Fish & Richardson P.C.

(57) ABSTRACT

Some embodiments of a medical device anchor system include an anchor device that secures a medical instrument (such as a catheter or the like) in place relative to a skin penetration point using subcutaneous anchors. In some implementations, the anchor device can be installed using a technique in which the subcutaneous anchors undergo relatively little or no flexing when being inserted through the skin into the subcutaneous region between the skin and underlying muscle tissue which may be occupied by fatty tissue.

17 Claims, 5 Drawing Sheets

(52) U.S. Cl.
CPC .. *A61M 39/0247* (2013.01); *A61M 2025/0286* (2013.01); *A61M 2039/0223* (2013.01); *A61M 2039/0261* (2013.01)

(56) References Cited

U.S. PATENT DOCUMENTS

| | | | |
|---|---|---|---|
| 3,059,645 A | 10/1962 | Hasbrouck et al. |
| 3,108,595 A | 10/1963 | Overment |
| 3,176,690 A | 4/1965 | H'Doubler |
| 3,308,819 A | 3/1967 | Arp |
| 3,630,195 A | 12/1971 | Santomieri |
| 3,677,250 A | 7/1972 | Thomas |
| 3,717,151 A | 2/1973 | Collett |
| 3,765,032 A | 10/1973 | Palma |
| 3,834,380 A | 9/1974 | Boyd |
| 3,856,009 A | 12/1974 | Winnie |
| 3,896,527 A | 7/1975 | Miller et al. |
| 3,938,529 A | 2/1976 | Gibbons |
| 4,043,346 A | 8/1977 | Mobley et al. |
| 4,114,618 A | 9/1978 | Vargas |
| 4,164,943 A | 8/1979 | Hill et al. |
| 4,248,224 A | 2/1981 | Jones |
| 4,309,994 A | 1/1982 | Grunwald |
| 4,397,647 A | 8/1983 | Gordon |
| 4,474,569 A | 10/1984 | Newkirk |
| 4,569,344 A | 2/1986 | Palmer |
| 4,592,356 A | 6/1986 | Gutierrez |
| 4,645,492 A | 2/1987 | Weeks |
| 4,665,906 A | 5/1987 | Jervis |
| 4,799,495 A | 1/1989 | Hawkins et al. |
| 4,804,359 A | 2/1989 | Grunwald et al. |
| 4,813,930 A | 3/1989 | Elliott |
| 4,936,823 A | 6/1990 | Colvin et al. |
| 4,986,810 A | 1/1991 | Semrad |
| 5,041,085 A | 8/1991 | Osborne et al. |
| 5,067,957 A | 11/1991 | Jervis |
| 5,122,122 A | 6/1992 | Allgood |
| 5,190,546 A | 3/1993 | Jervis |
| 5,256,146 A | 10/1993 | Ensminger et al. |
| 5,267,960 A | 12/1993 | Hayman et al. |
| 5,279,564 A | 1/1994 | Taylor |
| 5,312,337 A | 5/1994 | Flaherty et al. |
| 5,344,439 A | 9/1994 | Otten |
| 5,368,017 A | 11/1994 | Sorenson et al. |
| 5,378,239 A | 1/1995 | Termin et al. |
| 5,456,671 A | 10/1995 | Bierman |
| 5,496,277 A | 3/1996 | Termin et al. |
| 5,578,013 A | 11/1996 | Bierman |
| 5,597,378 A | 1/1997 | Jervis |
| 5,599,311 A | 2/1997 | Raulerson |
| 5,653,718 A | 8/1997 | Yoon |
| 5,681,288 A | 10/1997 | Schlitt |
| 5,688,247 A | 11/1997 | Haindl et al. |
| 5,702,371 A | 12/1997 | Bierman |
| 5,707,362 A | 1/1998 | Yoon |
| 5,722,959 A | 3/1998 | Bierman |
| 5,728,133 A | 3/1998 | Kontos |
| 5,741,234 A | 4/1998 | Aboul-Hosn |
| 5,746,720 A | 5/1998 | Stouder, Jr. |
| 5,755,697 A | 5/1998 | Jones et al. |
| 5,769,821 A | 6/1998 | Abrahamson et al. |
| 5,800,402 A | 9/1998 | Bierman |
| 5,810,781 A | 9/1998 | Bierman |
| 5,814,065 A | 9/1998 | Diaz |
| 5,827,230 A | 10/1998 | Bierman |
| 5,833,664 A | 11/1998 | Seare, Jr. |
| 5,833,667 A | 11/1998 | Bierman |
| 5,857,999 A | 1/1999 | Quick et al. |
| 5,921,965 A | 7/1999 | Blei |
| 5,928,266 A | 7/1999 | Kontos |
| 5,944,732 A | 8/1999 | Raulerson et al. |
| 5,947,931 A | 9/1999 | Bierman |
| 5,971,960 A | 10/1999 | Flom et al. |
| 5,989,265 A | 11/1999 | Bouquet De La Joliniere et al. |
| 6,213,979 B1 | 4/2001 | Bierman |
| 6,231,548 B1 | 5/2001 | Bassett |
| 6,290,676 B1 | 9/2001 | Bierman |
| 6,413,240 B1 | 7/2002 | Bierman et al. |
| 6,447,485 B2 | 9/2002 | Bierman |
| 6,540,693 B2 | 4/2003 | Burbank et al. |
| 6,572,588 B1 | 6/2003 | Bierman et al. |
| 6,582,388 B1 | 6/2003 | Coleman et al. |
| 6,582,403 B1 | 6/2003 | Bierman et al. |
| 6,663,600 B2 | 12/2003 | Bierman et al. |
| 6,679,851 B2 | 1/2004 | Burbank et al. |
| 6,695,861 B1 | 2/2004 | Rosenberg et al. |
| 6,770,055 B2 | 8/2004 | Bierman et al. |
| 6,896,665 B2 | 5/2005 | Picha et al. |
| 6,958,044 B2 | 10/2005 | Burbank et al. |
| 7,056,286 B2 | 6/2006 | Ravenscroft et al. |
| 2002/0068898 A1 | 6/2002 | McGuckin, Jr. et al. |
| 2002/0068899 A1 | 6/2002 | McGuckin, Jr. et al. |
| 2002/0120250 A1 | 8/2002 | Altman |
| 2002/0165489 A1 | 11/2002 | McGuckin, Jr. et al. |
| 2005/0043685 A1 | 2/2005 | Schinkel-Fleitmann |
| 2005/0187578 A1 | 8/2005 | Rosenberg et al. |
| 2005/0256458 A1 | 11/2005 | Howard et al. |
| 2005/0273058 A1 | 12/2005 | Bierman |
| 2007/0078397 A1 | 4/2007 | Weststrate |
| 2007/0225651 A1 | 9/2007 | Rosenberg et al. |
| 2008/0312599 A1 | 12/2008 | Rosenberg |
| 2009/0099524 A1 | 4/2009 | Kirchhofer et al. |
| 2009/0099527 A1 | 4/2009 | Rosenberg et al. |

FOREIGN PATENT DOCUMENTS

WO    WO 2005/039419    5/2005
WO    WO 2005/102438    11/2005

OTHER PUBLICATIONS

Johnson & Johnson web page printout, "The EndoANCHOR Firing Sequences" printed Sep. 13, 2005, 2 pages.
Johnson & Johnson web page printout, "The EndoANCHOR Comparative Summary" printed Sep. 13, 2005, 2 pages.
Web Page Printout of Statlock Device, publicly available before Sep. 29, 2010, 1 page.

SYSTEMS AND METHODS FOR ANCHORING MEDICAL DEVICES

CROSS-REFERENCE TO RELATED APPLICATIONS

This is a continuation of U.S. patent application Ser. No. 13/705,651 filed on Dec. 5, 2012 by Rosenberg et al., which is a continuation of U.S. patent application Ser. No. 12/893,783 filed on Sep. 29, 2010 by Rosenberg et al., the entire contents of which are incorporated herein by reference.

TECHNICAL FIELD

This document relates to a system and method for securing the position of a catheter or another medical instrument, for example, at a skin opening.

BACKGROUND

Venous, arterial, and body fluid catheters are commonly used by physicians. For example, such catheters may be used to gain access to the vascular system for dialysis, for introducing pharmaceutical agents, for nutrition or fluids, for hemodynamic monitoring, and for blood draws. Alternatively, catheters can be used for drainage of fluid collections and to treat infection. Following introduction into the patient, the catheter is secured to the patient. In some instances, the catheter is commonly secured to the patient using an adhesive tape on the skin or by suturing a catheter hub to the patient's skin. In other circumstances, the catheter may be secured to the patient using a subcutaneous anchor mechanism (such as an anchor sleeve equipped with anchors that are deployed using an external actuator handle or a separate delivery device).

SUMMARY

Some embodiments of a medical device anchor system include an anchor device that secures a medical instrument (such as a catheter or the like) in place relative to a skin penetration point using subcutaneous anchors that are readily inserted without the use of a deployment actuator. In some implementations, the anchor device can be installed using a technique in which the subcutaneous anchors undergo relatively little or no flexing when being inserted through the skin into the subcutaneous region (e.g., the region immediately under the skin and between the skin and underlying muscle tissue which may be occupied by fatty tissue). As such, the subcutaneous anchors of the anchor device may be inserted through the skin penetration point that is already occupied by the medical instrument while in a generally non-stressed or non-flexed shape. According to certain implementations of the installation technique, the subcutaneous anchors can also be shifted to a different orientation after installation into the subcutaneous region, yet the subcutaneous anchors may continue to be maintained in generally the same shape as during insertion through the skin penetration point. Accordingly, the subcutaneous anchors of the anchor device can be installed through the skin and into the subcutaneous region using a technique that reduces or eliminates flexing of the subcutaneous anchors, thereby permitting the use of more rigid materials for subcutaneous anchors (e.g., comprising materials without superelastic characteristics).

In particular embodiments, the anchor device may have a foldable configuration that facilitates both installation and removal of the subcutaneous anchors in a manner that reduces trauma to surrounding tissue near the skin penetration point. For example, the anchor device can be retained in a folded condition during installation of the subcutaneous anchors through the skin penetration point while each of the subcutaneous anchor tines has a first curved shape (e.g., a generally non-stressed or non-flexed shape). Also, the anchor device can be adjusted to a non-folded condition after installation of the subcutaneous anchors into the subcutaneous region, and each of the anchors tines can have generally the same first shape after the device is adjusted to the non-folded condition. The action of adjusting the anchor device to the non-folded condition can cause the subcutaneous anchors to shift relative to one another so that the subcutaneous anchors extend outwardly away from one another, yet may each maintain the first curved shape (e.g., generally non-stressed or non-flexed shape). During removal, the anchor device can be adjusted again to the folded condition so that the subcutaneous anchors are positioned side-by-side and extend generally in the same direction while also each maintaining generally the same first curved shape. In these circumstances, the subcutaneous anchors can be contemporaneously installed and removed from the skin penetration point in a manner that reduces the likelihood of damage to the tissue surrounding the skin penetration point while also reducing or eliminating flexing of the subcutaneous anchors.

Some embodiments of a method of using a medical anchor system may include the step of advancing an anchor device toward a skin penetration point while the anchor device is in a folded condition so that a plurality of subcutaneous tines of the anchor device are generally adjacent to each other and oriented to extend in substantially the same direction. The method may also include inserting the subcutaneous tines through the skin penetration point and into a subcutaneous region adjacent to an underside of a skin layer while the anchor device is in the folded condition. Each of the subcutaneous tines may have a curved shape which terminates at a tip of a free end during insertion through the skin penetration point. The method may further include adjusting the anchor device to a non-folded condition after the subcutaneous tines are inserted into the subcutaneous layer so that subcutaneous tines are in an anchored position in which the free ends of the subcutaneous tines extend generally away from one another. Also, the method may include securing a medical instrument to the anchor device after the subcutaneous tines are adjusted to the anchored position in the subcutaneous region.

These and other embodiments may provide one or more of the following advantages. First, some embodiments of an anchor system can retain a medical instrument in a desired position relative to a skin penetration point without necessarily requiring sutures or skin adhesives. Second, in some embodiments, the anchor device can be installed in accordance with a technique that reduces or eliminates the need to shift the subcutaneous anchors tines to or from a flexed or stressed configuration. As such, the anchor tines need not undergo substantial flexing during installation or removal. Third, in some embodiments the subcutaneous anchor tines need not have superelastic characteristics due to the installation and removal technique, so the subcutaneous anchor tines can comprise a generally less costly material (such as stainless steel or biocompatible polymers) rather than more costly materials required for superelastic flexing. Fourth, the subcutaneous anchors can be positioned distally of the retention portion that that readily mates with a medical instrument (such as a catheter), thereby enabling the subcutaneous anchors tines to be secured in the subcutaneous region under the skin while the catheter or other medical device is retained externally from the skin. Fifth, in some embodiments, the anchor device may be adjusted between a folded configuration and a non-folded configuration so that the subcutaneous anchors are arranged side-by-side and extend in generally the same direction during both installation through and removal from the skin penetration point. In these circumstances, the subcutaneous anchors may be readily installed and removed from the skin penetration without the need for a separate external actuator or delivery device.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
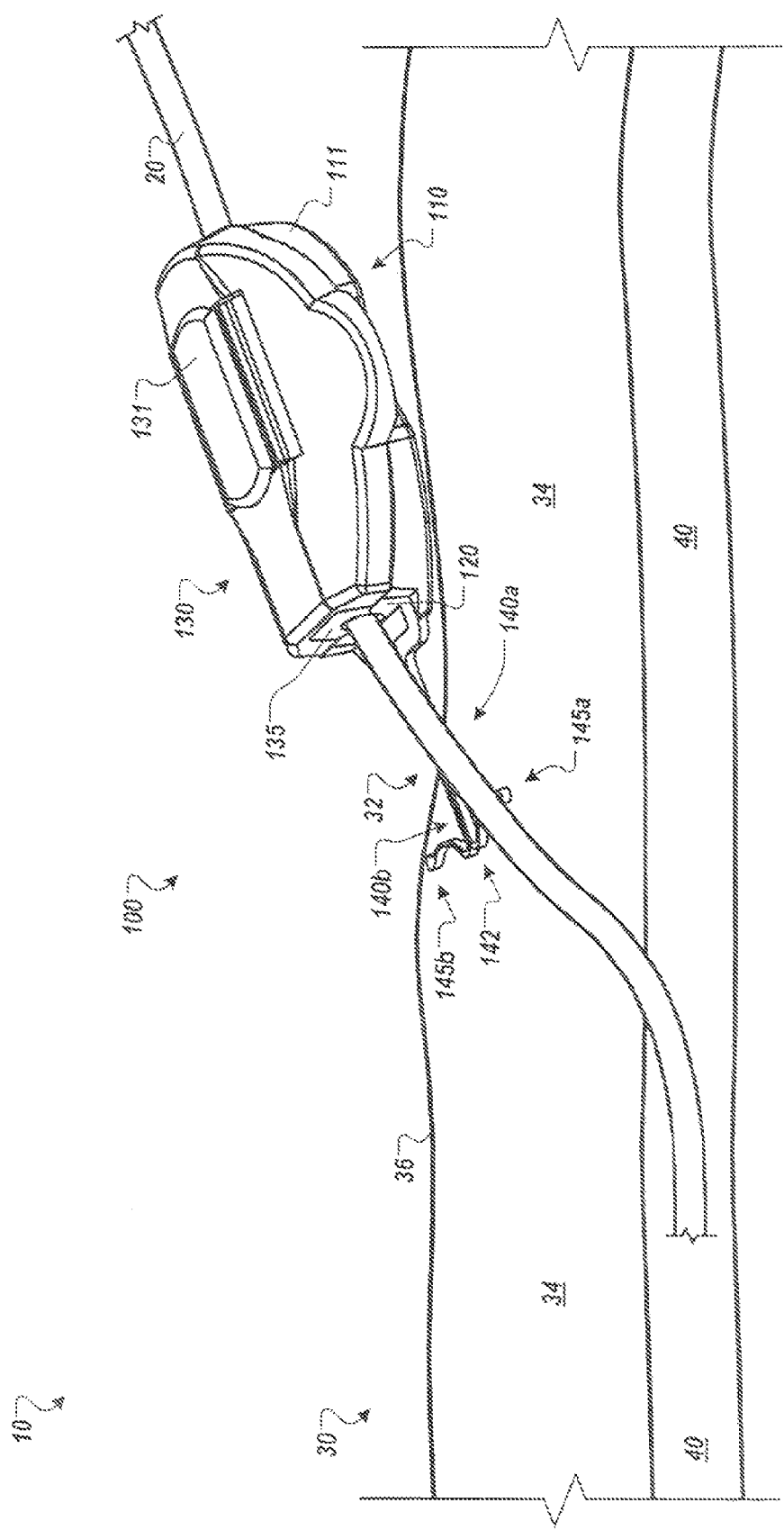
FIG. 1 is a perspective view of an anchor device with a portion of the device located in a subcutaneous region, in accordance with some embodiments.

Referring to FIG. 1, some embodiments of a medical device anchor system 10 include an anchor device 100 that releasably retains a medical instrument 20 (e.g., depicted as a catheter in this embodiment) in an operative position relative to a portion of skin 30 (e.g., relative to a skin penetration point 32). The anchor device 100 may include a base 110 and a cap assembly 130. The base 110 may include a retainer body 111 and one or more anchors 140a-b that extend distally from the retainer body 111 for deployment in a subcutaneous layer 34. As described in more detail below in connection with FIGS. 4-7, the anchor device can be installed into a skin penetration point 32 in accordance with a technique that reduces or eliminates the need to shift subcutaneous anchors tines 145a-b of the anchors 140a-b to or from a flexed or stressed configuration. As such, the anchor tines need not undergo substantial flexing during installation or removal. In these circumstances, the subcutaneous anchors may be both installed and removed from the skin penetration advantageously without the need for an external actuator handle or delivery device to deploy the subcutaneous tines.

As shown in FIG. 1, after installation of the subcutaneous anchor tines 145a-b into the subcutaneous layer 34, the base 110 can receive the medical instrument 20, and the cap assembly 130 can be removably coupled to the base 110 to secure the medical instrument 20 in a generally fixed position relative to the base 110. The base 110 and the cap assembly 130 can include gripping members 120 and 135, respectively (refer also to FIGS. 2-3). When the cap assembly 130 is coupled to the base 110, the gripping members 120 and 135 can releasably engage with an outer surface of the medical instrument 20. The medical instrument 20 can extend from the gripping members 120 and 135 and through a skin penetration point 32 in a patient's skin 30, while the retainer body 111 and the gripping members 120 and 135 remain outside of the skin 30. IN some embodiments, the skin penetration point 32 may be defined by a small incision, a puncture, or the like.

As described in more detail below, the anchor device 100 can secure the catheter 20 in the operative position relative to the penetration point 32 without necessarily requiring sutures or adhesive tapes bonded to the skin. For example, the base 110 can include the one or more anchors 140a and 140b that extend distally from the retainer body 111 so as to penetrate through the same skin opening as the medical instrument 20. The anchors 140a and 140b can include the tines 145a and 145b that, after insertion, reside in the subcutaneous region 34 so as to secure the position of the anchor device 100—and the medical instrument 20 retained therein—relative to the penetration point 32.

Figure 2:
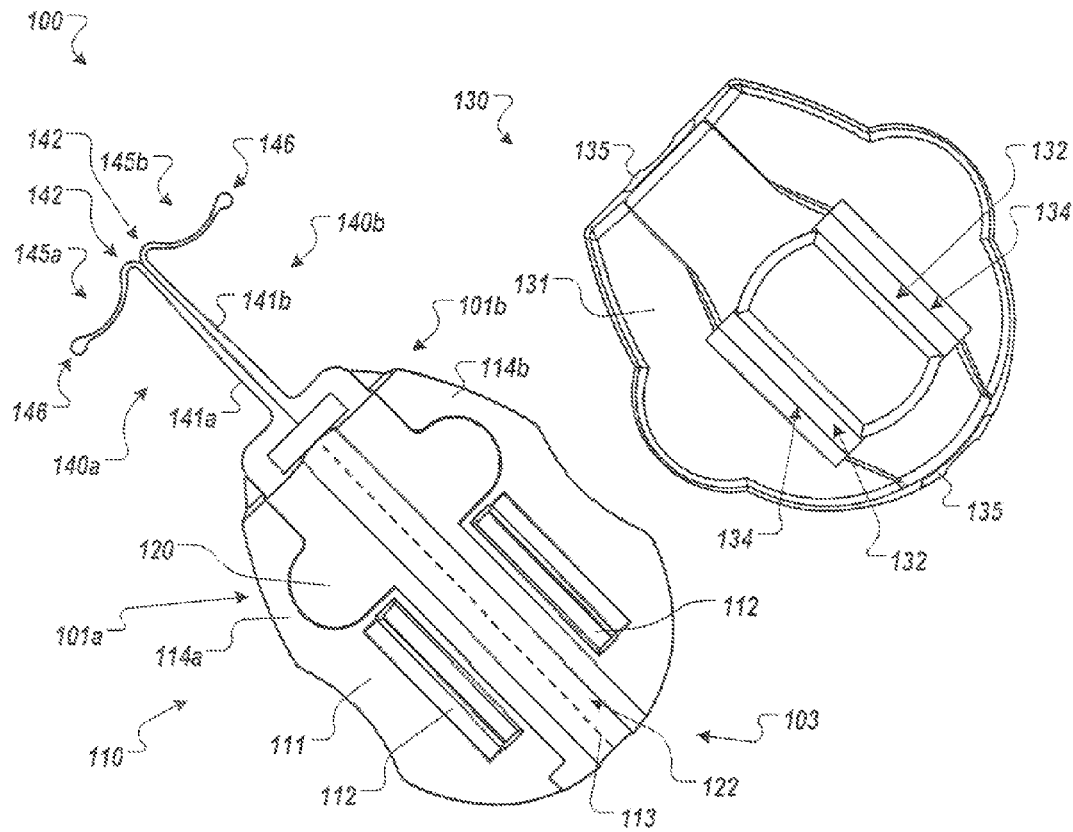
FIGS. 2-3 are top and front views, respectively, of the anchor device of FIG. 1 with the medical device retention portion in an open and deployed configuration.
Figure 3:
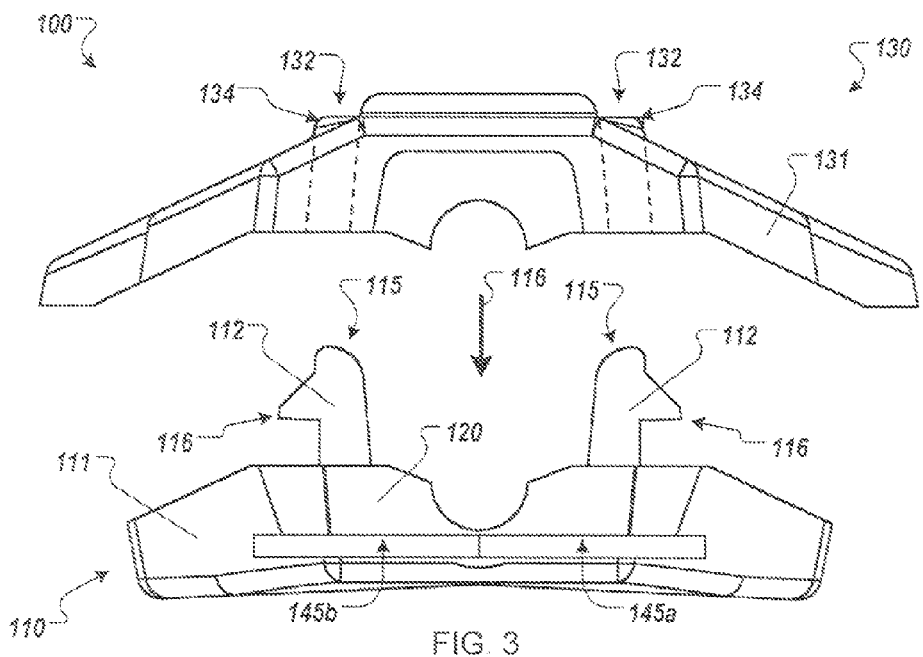

Referring now to FIGS. 1-3, in some embodiments, the medical instrument 20 can include a catheter to be inserted through the penetration point 32 of the skin 30 as part of a medical procedure. For example, in the embodiment depicted in FIG. 1, a central venous catheter 20 can be inserted into a percutaneous opening surgically formed in the skin (e.g., penetration point 32), to the underside of the skin 30, and into a vein 40 to provide vascular access for delivering medications or minimally invasive devices into a patient. After placement of the catheter 20, the base 110 of the anchor device 100 can approach the penetration point 32 such that the free ends of the tines 145a-b are contemporaneously inserted through the penetration point 32 while the tines 145a-b are in a generally side-by-side condition (refer, for example, to FIGS. 4-5). As the anchor device 100 is inserted through the penetration point 32, the tines 145a-b are maintained in a generally non-stressed configuration (e.g., a first shape or a steady-state shape) while passing through the penetration point 32 in a manner that reduces the likelihood of trauma to the surrounding skin tissue. As the tines 145a-b are collectively advanced through the penetration point 32, the free ends of the tines 145a-b are moved beneath the dermal skin layers 36 of the skin 30. When the tines 145a-b reach the subcutaneous region 34, the tines 145a-b can be shifted relative to one another so that the tines 145a-b extend outwardly away from one another while each tine 145a-b retains the generally non-stressed configuration (e.g., the first shape or the steady-state shape). Thus, as described in more detail below in connection with FIGS. 4-7, the anchor device 100 can be installed in accordance with a technique that reduces or eliminates the need to shift the subcutaneous anchors tines 145a-b to or from a flexed or stressed configuration during the passage through the skin penetration point. As such, the subcutaneous anchors tines 145a-b need not undergo substantial flexing during installation or removal, and in some embodiments, the subcutaneous anchors tines 145a-b can comprise a generally less costly material (such as stainless steel or biocompatible polymers) rather than more costly materials required for super-elastic flexing.

Referring now to FIG. 2, each of the anchors 140a-b may be designed such that the tines 145a-b has a first shape with a convex curvature that abuts against the underside of the dermal layers 36 in a manner that reduces the likelihood of the tine tips 146 puncturing the underside of the dermal layers 36. Preferably, the tine tips 146 are rounded or otherwise non-sharp so as to further protect the underside of the dermal layers. When the tines 145a-b of the anchors 140a-b are deployed in the subcutaneous region 34, the cap assembly 130 can be removably coupled to the base 110 (refer, for example to FIG. 7), compressing the gripping portions 120 and 135 onto the medical instrument 20 and causing the gripping portions 120 and 135 to releasably engage with an outer surface of the medical instrument 20. In this way, the anchor device 100 can be secured to the patient without the retainer body 111 penetrating though the skin 30 of the patient and without necessarily requiring sutures or adhesive tapes bonded to the skin 30.

Referring now to FIGS. 2-3, some embodiments of the anchor device 100 can include structures designed to mate with portions of the medical instrument 20 to be retained by the anchor device 100. The anchor device 100 can include the gripping members 120 and 135 used to secure the catheter 20 (or other medical instrument) relative to the skin penetration point 32. For example, after the catheter 20 is delivered into the targeted vein 40 (or other bodily lumen) and after the tines 145a-b are anchored in the subcutaneous region 34, the cap assembly 130 can be removably coupled to the base 110, compressing the gripping members 120 and 135 to temporarily engage with the outer surface of the catheter 20. In this way, the anchor device 100 can be transitioned from the open configuration (shown in FIG. 2-3) to the closed configuration (shown in FIG. 1) to thereby secure the catheter 20 with the gripping members 120 and 135. As described in more detail below, the retainer body 111 can include locking tabs 112 that can pass through openings 132 in the cap 131 and positively engage at least a portion of perimeters 134 of the openings 132, thereby removably coupling the cap assembly 130 to the base 110.

Still referring to FIGS. 2-3, the anchor device 100 can include features that facilitate separation from the catheter 20, which can permit the catheter 20 and anchor device 100 to be removed from the skin 30 independently of each other. For example, the tabs 112 may be disengaged from the cap assembly 130 to decouple the cap assembly 130 from the base 110. Once the cap assembly 130 is removed, the gripping members 120 and 135 can release from the catheter 20, thereby allowing the catheter 20 to be moved relative to the anchor device 100. As such, the catheter 20 can be moved independently from the anchor device 100, for example, to withdraw the catheter 20 from the patient while at least a portion of the anchor device 100 remains secured to the skin 30.

Some embodiments of the anchor device 100 can include structures configured to mate with portions of the medical instrument 20 to be retained by the anchor device 100. For example, when the anchor device is in the closed configuration (as depicted in FIG. 1), the gripping members 120 and 135 can define a channel 122 (illustrated in FIG. 2) that extends longitudinally from the proximal portion 103 of the anchor device 100 toward the anchors 140a-b. The channel 122 can be configured to complement an outer surface of the catheter 20 or other medical instrument to be anchored by the device 100. For example, during installation of the anchor device 100, the anchors 140a-b are directed toward the penetration point 32 through which the catheter 20 passes. When the tines 145a-b are anchored in the subcutaneous region 34, the cap assembly 130 can be removably coupled to the base 110, which transitions the anchor device 100 to the closed configuration. As such, the catheter 20 can extend though the channel 122 when the subcutaneous tines 145a-b are arranged in the region immediately under the skin 30.

In some embodiments, particular features of the anchor device 100 can removably couple the base 110 to the cap assembly 130. In the example depicted in FIG. 3, the cap assembly 130 can be moved toward the base 110 (e.g., in the direction depicted by arrow 106) to direct the tabs 112 toward to the openings 132. When the diagonal faces of the tabs 112 contact the perimeters 134, the tabs 112 are stressed such that the tips 115 of the tabs 112 move closer to each other. When the face 135 moves beyond the engagement fingers 116, the tabs 112 can outwardly toward their unstressed positions to releasably engage the perimeters 134. When in this closed configuration, the cap assembly 130 and base 110 can apply a compressive force from the gripping members 120 and 135 to the catheter 20 in the channel 122, thereby applying a frictional holding force to the catheter 20 or medical instrument therein.

In some embodiments, the holding force that secures the catheter 20 to the anchor device 100 can be released by separating the cap assembly 130 from the base 110. The cap assembly 130 can be separated from the base 110 by disengaging the locking tabs 112 from the cap assembly 130. For example, the base 110 can be separated from the cap assembly 130 by applying pressure to the locking tabs 112 to move the tips 115 closer to each other. When the engagement portions 116 of the tabs 112 move inside the openings 132 in the cap 131, the retainer portions 120 and 135 force the cap assembly 130 away from the base 110 and the cap assembly 130 becomes decoupled from the base 110, thus transitioning the anchor device 100 to the open configuration (FIGS. 2-3). When the anchor device 100 is in the open configuration (e.g., with the cap 130 removed), the catheter 20 can be moved relative to the anchor device 100.

Referring now to FIGS. 4-7, the anchor device 100 can be installed using a technique in which the subcutaneous anchor tines 145a-b undergo relatively little or no flexing when being inserted through the skin penetration point 32 into the subcutaneous layer 32 between the skin 30 and the underlying muscle tissue. As such, the subcutaneous anchors tines 145a-b can be inserted through the skin penetration point 32 that is already occupied by the catheter 20 while each tine 145a-b is maintained in a generally non-stressed or non-flexed shape. Also, as described in FIGS. 6-7, the subcutaneous anchors tines 145a-b can also be shifted to a different orientation after installation into the subcutaneous region 34, yet the tines 145a-b may continue to be maintained in the generally non-stressed or non-flexed shape. Accordingly, the subcutaneous anchors of the anchor device can be installed through the skin and into the subcutaneous region using a technique that reduces or eliminates flexing of the subcutaneous anchors, thereby permitting the use of more rigid materials for subcutaneous anchors (e.g., comprising materials without superelastic characteristics).

Figure 4:
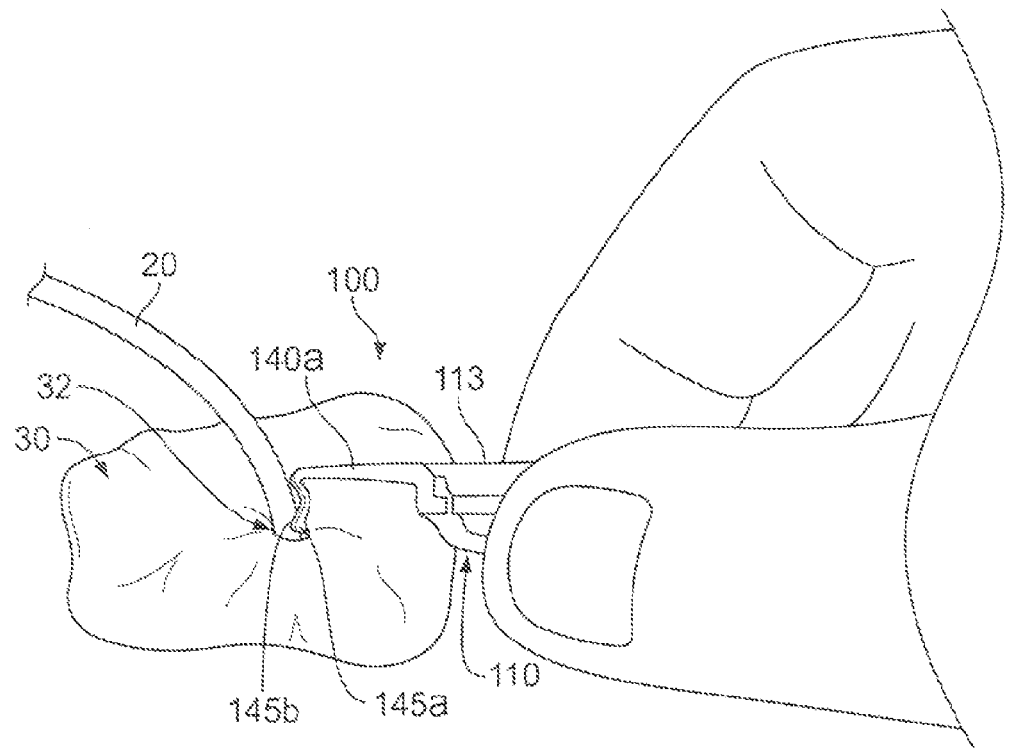
FIGS. 4-7 are perspective views of a method of using an anchor system, including the anchor device of FIG. 1, for use in securing the position of a medical instrument.

In this embodiment, the anchor device 100 may include features that allow the individual anchors 140a-b to be moved relative to each other so as to facilitate both insertion and removal of the anchor device 100 through the skin penetration point. For example, the anchor device 100 may have a foldable configuration in which a first portion of the base 110 is pivotably coupled to a second portion of the base 110. The anchor device 100 can include a left portion 101a and a right portion 101b (refer to FIG. 2), which can be flexibly pivoted with respect to each other along a fold line 113 (refer to FIG. 2) extending longitudinally through the retainer body 111. The left portion 101a can include a left retainer body portion 114a (refer to FIG. 2) fixedly coupled to the anchor 140a, and the right portion 101b can include a right retainer body portion 114b (refer to FIG. 2) fixedly coupled to the anchor 140b. Thus, as shown in FIG. 4, when the left and right retainer body portions 114a and 114b are pivoted about the fold line 113, the two anchors 140a-b likewise pivot relative to one another. This process can cause the anchor device to transition from a folded condition (shown in FIGS. 4-5), in which the tines 145a-b are generally adjacent to each other and oriented to extend in substantially the same direction, to a non-folded condition (shown in FIGS. 6-7 and in FIG. 1), in which the tines 145a-b extend generally away from one another. In the depicted embodiment, the tines 145a-b can be rotated about 75-degrees to about 105-degrees, and preferably about 90-degrees, during the transition between the folded condition and the non-folded condition. As described in more detail below, the anchor device 100 can be arranged in the folded condition during both insertion and removal of the subcutaneous tines 145a-b so as to reduce the likelihood of the tines 145a-b causing damage to the skin 30.

In particular embodiments, a method of using the medical anchor system (including the anchor device 100) may include an advantageous insertion technique. As shown in FIG. 4, the method may include a step of inserting a medical instrument (such as catheter 20) through the skin penetration point 32 (e.g., a puncture opening or incision) of the patient's skin 30. One example of the catheter 20 being inserted through the penetration point 32 is depicted in FIG. 4. In this embodiment, the catheter 20 may include a central venous catheter that extends from a location external to the skin 30, through the skin penetration point 32, and into a blood vessel 40 (FIG. 1) underlying the skin 30 and subcutaneous layer 34.

As shown in FIG. 4, after the catheter 20 or other medical instrument is inserted so that it occupies the skin penetration point 32, the method may include the step of advancing the anchor device 100 toward the skin penetration point 32 while in the folded condition. As previously described, when the base 110 of the anchor device 100 is in the folded condition, the subcutaneous tines 145a-b are generally adjacent to each other and oriented to extend in substantially the same direction. As such, the tips 146 of the subcutaneous tines 145a-b can located in a side-by-side position so that the tips 146 can be contemporaneously advanced to the skin penetration point 32 that is already occupied by the catheter 20 to be anchored. As described in more detail below, the anchor device 100 may be equipped with a clip device 160 or 170 (FIG. 8) or a snap connector 180a-b (FIG. 9) that retains the base 110 in the folded condition prior to insertion of the subcutaneous tines 145a-b.

Figure 5:
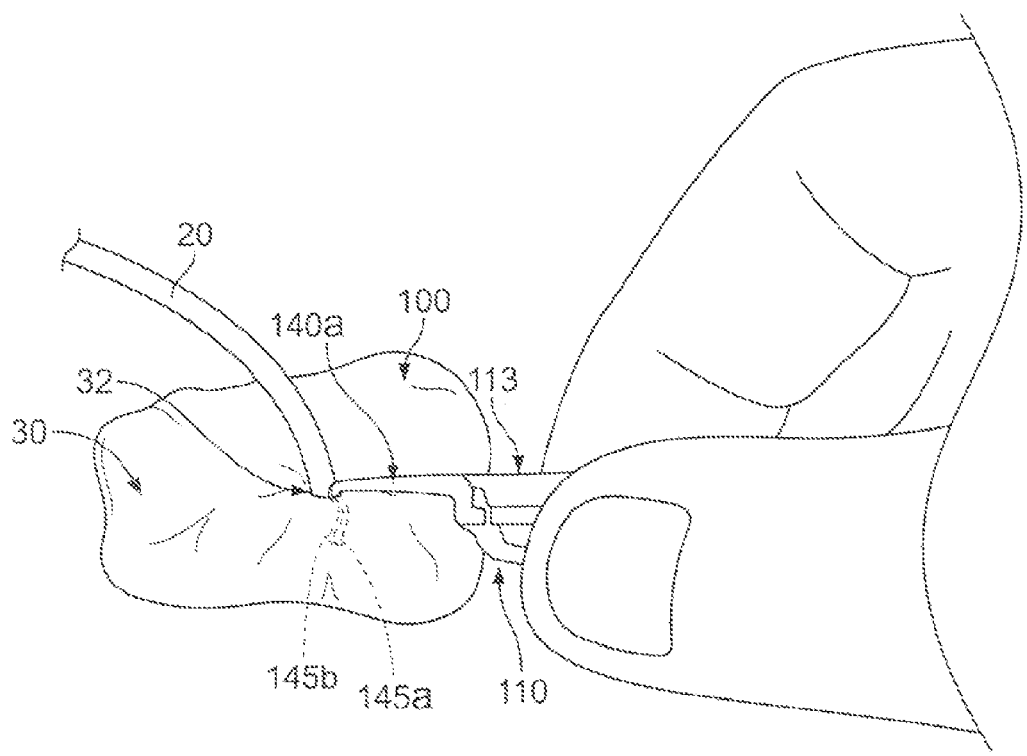

As shown in FIG. 5, the method may also include the step of inserting the subcutaneous tines 145a-b through the skin penetration point 32 while the base 110 of the anchor device 100 is in the folded condition. In such circumstances, the tips 146 of the subcutaneous tines 145a-b are generally adjacent to each other so that they can be the first portion of the subcutaneous tines 145a-b to initially advance through the skin penetration point 32 and into the subcutaneous layer 34. Because the subcutaneous tines 145a-b are generally adjacent to each other and oriented to extend in substantially the same direction, the subcutaneous tines 145a-b can be simultaneously inserted while being maintained in a non-stressed configuration. For example, the subcutaneous tines 145a-b are not necessarily forced into a flexed or stressed configuration by another component of the anchor system 10 during insertion of the subcutaneous tines 145a-b. In particular embodiments, the subcutaneous tines 145a-b are inserted through the skin penetration point 32 while the user grasps the base 110 of the anchor device 100 and applies a downward force until the convexly curved body portions of the subcutaneous tines 145a-b are positioned below the surface of the skin 30 (while the remainder of the anchor device 100 resides external to the skin 30).

Figure 6:
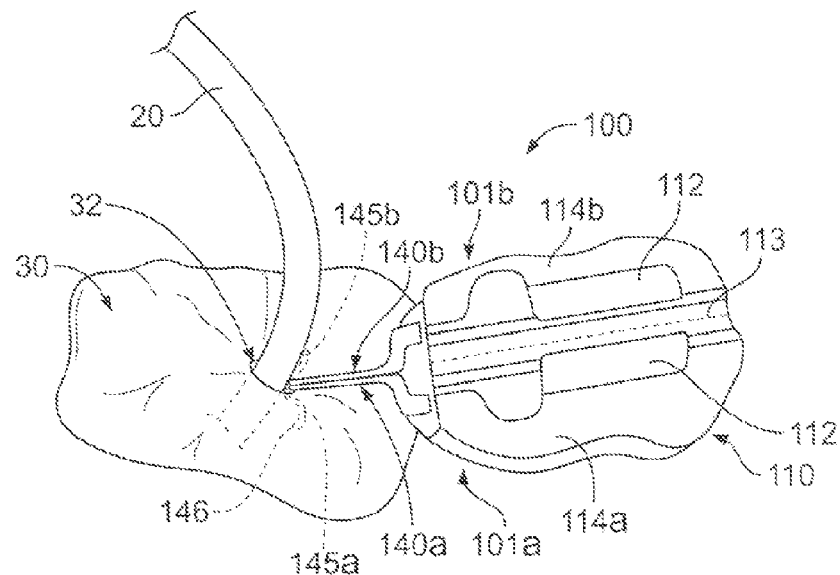

As shown in FIG. 6, the method may also include adjusting the anchor device 100 to the non-folded condition after the subcutaneous tines 145a-b are inserted into the subcutaneous layer 34. As previously described, the free ends of the subcutaneous tines 145a-b extend generally away from one another when the anchor device 100 is shifted to the non-folded condition. In such circumstances, the subcutaneous tines 145a-b are oriented in an anchored position in the subcutaneous layer 34 so as to anchor the retention portion 111 relative to the skin penetration point 32 that is occupied by the catheter 20. When in the anchored position, each of the tines 145a-b can be maintained at generally the same shape as when they were inserted through the skin penetration point (e.g., the generally non-stressed shape in which in which no other components of the anchor system 10 are forcing the tines 145a-b to flex). Accordingly, the convex curvature of the tines 145a-b abuts against the underside of the skin 30 in a manner that reduces the likelihood of the tine tips 146 puncturing the underside of the dermal layers 36. As previously described, the tine tips 146 are rounded or otherwise non-sharp so as to further protect the underside of the dermal layers.

Figure 7:
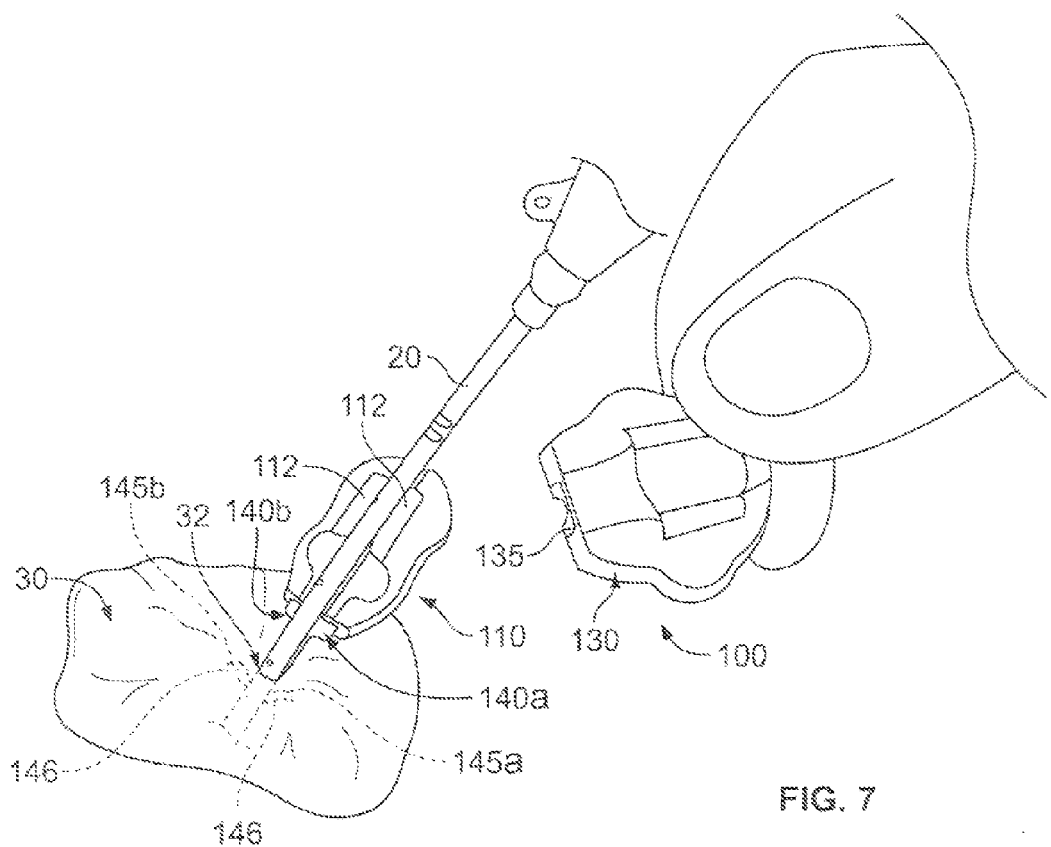

As shown in FIG. 7, the method may also include securing the catheter 20 to the anchor device 100 after the subcutaneous tines 145a-b are anchored in the subcutaneous layer 34. In this embodiment, the portion of the catheter 20 that is external to the skin 30 can be positioned in the channel 122 (FIG. 2) of the base 110. The cap assembly 130 can be removably coupled to the base 110 (refer, for example to FIG. 1) so that the gripping portions 120 and 135 of the anchor device 100 releasably engage with the outer surface of the catheter 20. In such embodiments, the anchor device 100 can be secured to the patient without the retainer body 111 penetrating though the skin 30 of the patient and without necessarily requiring sutures or adhesive tapes bonded to the skin 30. As previously described in connection with FIGS. 2-3, the cap assembly 130 can be moved toward the base 110 (e.g., in the direction depicted by arrow 106) to close the anchor device 100 around the portion of the catheter that is external to the skin 30. When in this closed configuration, the cap assembly 130 and base 110 can apply a compressive force from the gripping members 120 and 135 to the catheter 20, thereby applying a frictional holding force to the catheter 20 or medical instrument therein.

The method may further include the step of anchoring the catheter 20 to the skin penetration point 32 using the anchor device 100 during delivery of treatment through the catheter 20. For example, as shown in FIG. 1, the anchor device 100 can releasably anchor the catheter 20 to the skin penetration point 32 while the catheter 20 resides in a selected blood vessel 40 to deliver a particular treatment (e.g., to deliver a fluid, to extract a fluid, to deliver an instrument or implant, or the like). As shown in FIG. 1, the subcutaneous tines 145a-b serve to secure the anchor device 100 (and the catheter 20 secured thereto) to the skin penetration point 32 by abutting against an underside of the skin 30.

The method may also include steps for removing the anchor device 100. During removal, the anchor device 100 can be adjusted to the folded condition once again so as to facilitate a prompt removal of the subcutaneous tines 145a-b from the skin penetration point. Accordingly, the removal process will be substantially the opposite order of steps as shown in FIGS. 4-7. For example, during removal, the cap assembly 130 can be detached from the base 110 so that the catheter 20 can be freed from the base. The catheter 20 may be withdrawn from the skin penetration point before the subcutaneous tines 145a-b are removed, or alternatively, the catheter 20 may remain in place while the subcutaneous tines 145a-b are removed first. After the base 100 is free from the cap assembly 130 (in a condition similar to that of FIG. 6), the base can be adjusted to the same folded condition employed during the insertion technique (refer to FIG. 5). In such circumstances, the subcutaneous tines 145*a-b* are generally adjacent to each other and oriented to extend in substantially the same direction. As such, the subcutaneous tines 145*a-b* can be simultaneously removed while being maintained in a non-stressed configuration (refer to FIG. 4). Such a removal process can be used to reduce the cross sectional area of the portion of the anchors 140*a-b* being withdrawn through the skin penetration point 32, thereby reducing the likelihood of damaging the surrounding skin tissue 30 during removal of the anchors 140-*b*.

Accordingly, the anchor device 100 may have a foldable configuration that facilitates both installation and removal of the subcutaneous anchors 140*a-b* in a manner that reduces trauma to surrounding tissue near the skin penetration point 32.

Figure 8:
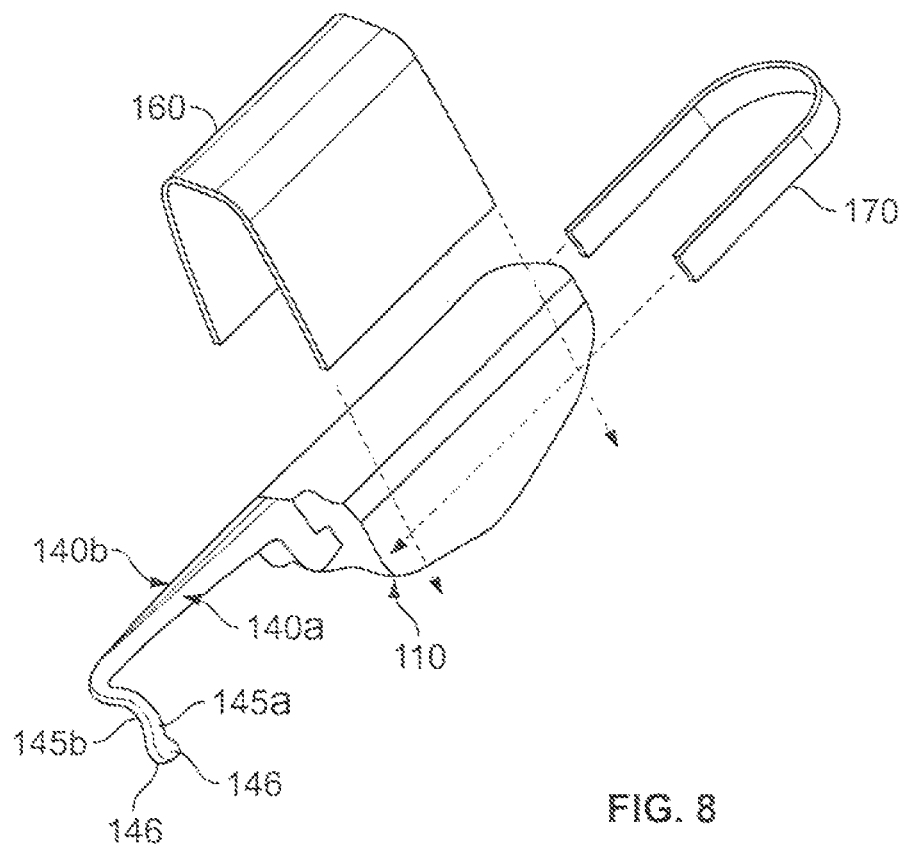
FIG. 8 is a perspective view of an anchor device for use in the method of FIGS. 4-7, including a mechanism for retaining the anchor device in a folded condition in accordance with some embodiments.
Figure 9:
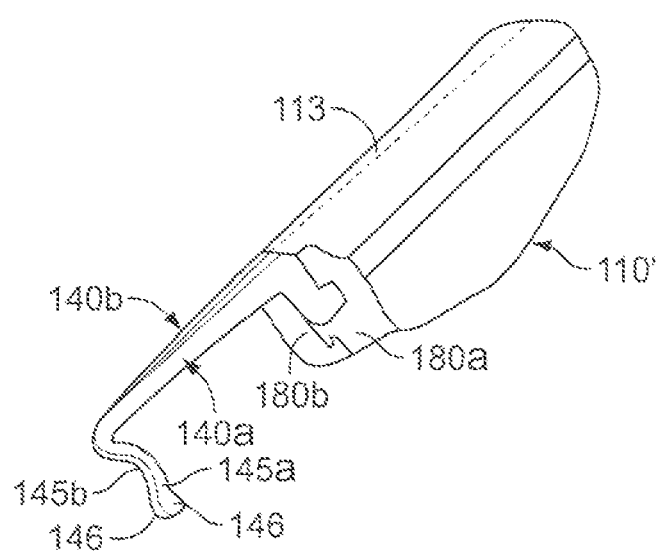
FIG. 9 is a perspective view of an anchor device for use in the method of FIGS. 4-7, including another mechanism for retaining the anchor device in a folded condition in accordance with other embodiments.

Referring now to FIGS. 8-9, some embodiments of the anchor device 100 may include one or more structures that releasably retain the base 110 of the anchor device 100 in the folded condition. For example, the anchor device 100 may be provided in a sterile package while being retained in the folded condition. In such circumstances, a user can readily remove the device 100 and begin to insert the subcutaneous tines 145*a-b* through the skin penetration point 132 (as shown in FIGS. 4-5) without having to manually adjust the base 110 to the folded condition. After insertion the subcutaneous tines 145*a-b* into the subcutaneous layer 32, the user can then remove or separate the one or more structures that releasably retain the base 110 of the anchor device 100 in the folded condition. The anchor device 100 can be biased toward the non-folded condition (as shown in FIG. 6) upon removal of the one or more structures.

As shown in FIG. 8, the some embodiments of the anchor device 100 may include one or more removable structures that releasably retain the base 110 of the anchor device 100 in the folded condition. For example, the removable structure may include a U-shaped clip device 160 that slidably engages the base 100. The U-shaped clip device 160 can be readily removed from the base 110 by sliding the clip device 160 in a lateral direction generally perpendicular to the fold line 113 of the anchor device 100. In a second example, the removable structure may include a different U-shaped clip device 170 that slidably engages the base 100 from a longitudinal direction. The U-shaped clip device 170 can be readily removed from the base 110 by sliding the clip device 160 in a longitudinal direction that is generally parallel to the fold line 113 of the anchor device 100.

As shown in FIG. 9, the some embodiments of the anchor device 100 may include one or more structures that are integrally formed with another component of the anchor device 100 so as to releasably retain the base 110 of the anchor device 100 in the folded condition. For example, the structure may include a snap-fit connector having mating components 180*a-b* that secure together when the base 110 is in the folded condition. The snap-fit connector components 180*a-b* may include a mating tongue or extension that mates with a groove or detent. When the user is ready to adjust the anchor device 100 to the non-folded condition, the snap-fit connector components 180*a-b* can be manually separated by application of a low separation force from the user. The U-shaped clip device 160 can be readily removed from the base 110 by sliding the clip device 160 in a lateral direction generally perpendicular to the fold line 113 of the anchor device 100.

In these embodiments illustrated in FIGS. 8-9, the anchor device 100 may be provided in a sterile package while being retained in the folded condition by one or more of the clip device 160 or 170 or the snap-fit connector components 180*a-b*. From there, a user can readily remove the device 100 and begin to insert the subcutaneous tines 145*a-b* through the skin penetration point 132 without being required to manually adjust the base 110 to the folded condition.

A number of embodiments of the invention have been described. Nevertheless, it will be understood that various modifications may be made without departing from the scope of the invention. Accordingly, other embodiments are within the scope of the following claims.

What is claimed is:

1. An anchor device for releasably securing to an external portion of a medical instrument while another portion of the medical instrument occupies a skin penetration point, the anchor device comprising:
   first and second anchors each having a longitudinal shaft portion and a subcutaneous tine configured to be deployed through the skin penetration point and into a subcutaneous region along an underside of a skin layer; and
   a retainer base to releasably secure with the external portion of the medical instrument, the retainer base being in a folded condition about a longitudinal fold axis of the retainer base prior to deployment of the subcutaneous tines through the skin penetration point such that the subcutaneous tines are positioned generally adjacent to each other and oriented to extend in substantially the same direction,
   wherein the retainer base is adjustable to a non-folded condition about the longitudinal fold axis of the retainer base after deployment of the subcutaneous tines through the skin penetration point so that the subcutaneous tines are in an anchored position.

2. The device of claim 1, further comprising a mechanism that releasably retains the retainer base in the folded condition, wherein the retainer base is biased to return to the non-folded condition.

3. The device of claim 2, the retainer base is adjustable to a non-folded condition about the longitudinal fold axis of the retainer base in response to releasing the mechanism from the retainer base so that retainer base is urged to the non-folded condition by a spring bias force.

4. The device of claim 1, the retainer base includes a first body portion that is pivotably coupled to a second body portion about the longitudinal fold axis of the retainer base, the longitudinal fold axis of the retainer base being defined by an elastically flexible longitudinal folding region positioned between the first body portion and the second body portion.

5. The device of claim 4, wherein the longitudinal shaft portion of each of the first and second anchors having a distal end portion that is coupled with a respective one of the subcutaneous tines, the longitudinal shaft portion of the first anchor being mechanically coupled to the first body portion of the retainer base, and the longitudinal shaft portion of the second anchor being mechanically coupled to the second body portion of the retainer base.

6. The device of claim 4, further comprising a cap that is releasably attachable to the retainer base so as to define a channel therebetween that is sized to retain the external portion of the medical instrument.

7. The device of claim 6, wherein the retainer base and the cap each include a gripper member configured to frictionally engage the external portion of the medical instrument.

8. The device of claim 6, wherein the cap includes: a first mounting structure to releasably attach to a first mating structure of the first body portion of the retainer base, and a second mounting structure to releasably attach to a second mating structure of the second body portion of the retainer base, the first and second mating structures being positioned on opposite sides of the longitudinal fold axis of the retainer base.

9. The device of claim 1, wherein each of the subcutaneous tines has longitudinal convexly curved portion extending toward a tip at a free end, the longitudinal convexly curved portion being configured to abut against the underside of the skin layer.

10. The device of claim 9, wherein each of the tips at the free ends is rounded or other non-sharp so as to protect the underside of the skin layer.

11. The device of claim 1, wherein during the retainer base is in the folded condition about the longitudinal fold axis of the retainer base prior to deployment of the subcutaneous tines through the skin penetration point such that the subcutaneous tines are arranged in a side-by-side position so that tips of the subcutaneous tines are simultaneously insertable through the skin penetration point while the skin penetration point is already occupied by the catheter.

12. The device of claim 1, wherein the subcutaneous tines are configured to be deployed through the skin penetration point while in a generally non-stressed and non-flexed shape.

13. The device of claim 12, wherein the subcutaneous tines are configured to have the same generally non-stressed and non-flexed shape after the subcutaneous tines are adjusted to the anchored position in the subcutaneous region.

14. The device of claim 1, wherein the medical instrument comprises a catheter.

15. The device of claim 1, wherein the subcutaneous tines comprise flexible subcutaneous tines.

16. The device of claim 1, wherein the longitudinal shaft portion of the first anchor is positioned on an opposite side of the longitudinal fold axis from the longitudinal shaft portion of the second anchor, and wherein the longitudinal shaft portion of each of the first and second anchors extends distally in a longitudinal direction from a distalmost end of the retainer base.

17. The device of claim 1, wherein in the anchored position the subcutaneous tines extend generally away from one another.

* * * * *